BEST AVAILABLE COPY

United States Patent [19]

Harris et al.

[11] Patent Number: 4,661,285

[45] Date of Patent: Apr. 28, 1987

[54] BALSAMIC FRAGRANCE COMPOSITION AND PROCESS FOR PREPARATION

[75] Inventors: Eugene G. Harris, West Chester; Jane C. Mueninghoff, St. Bernard, both of Ohio

[73] Assignee: National Distillers and Chemical Corporation, New York, N.Y.

[21] Appl. No.: 860,268

[22] Filed: May 5, 1986

[51] Int. Cl.[4] .......................... A61K 7/46; C11B 9/00

[52] U.S. Cl. ................................ 252/522 R; 560/120; 562/505

[58] Field of Search .................... 252/522 R; 560/120; 562/502

[56] References Cited

U.S. PATENT DOCUMENTS

| | | | |
|---|---|---|---|
| 3,637,801 | 1/1972 | Kuder | 560/120 |
| 3,641,144 | 2/1972 | Kuder | 562/510 |
| 3,689,537 | 9/1972 | Kuder | 562/502 |
| 4,442,025 | 4/1984 | Blelens et al. | 252/522 R |

*Primary Examiner*—Werren B. Lone

*Attorney, Agent, or Firm*—Kenneth D. Tremain; Gerald A. Baracka

[57] ABSTRACT

Balsamic fragrance compositions having fruity, fir needle notes with the character of fir balsam absolute are produced by reacting camphene, and ethylhaloacetate and di-t-butyl peroxide; reacting the mixture obtained therefrom with zinc and water; vacuum distilling the resulting product; and collecting a specified fraction.

8 Claims, 3 Drawing Figures

GLC PROFILE FOR EXAMPLE I(4)

GLC PROFILE FOR EXAMPLE II

BEST AVAILABLE COPY
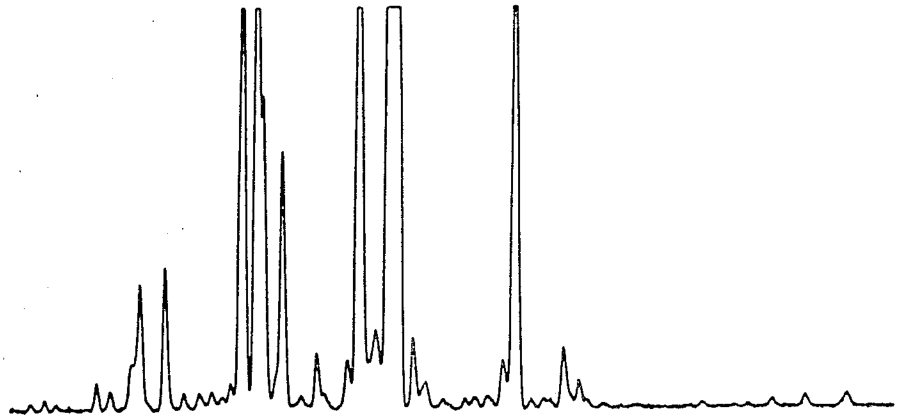
FIG. 1 - GLC PROFILE FOR EXAMPLE I(d)
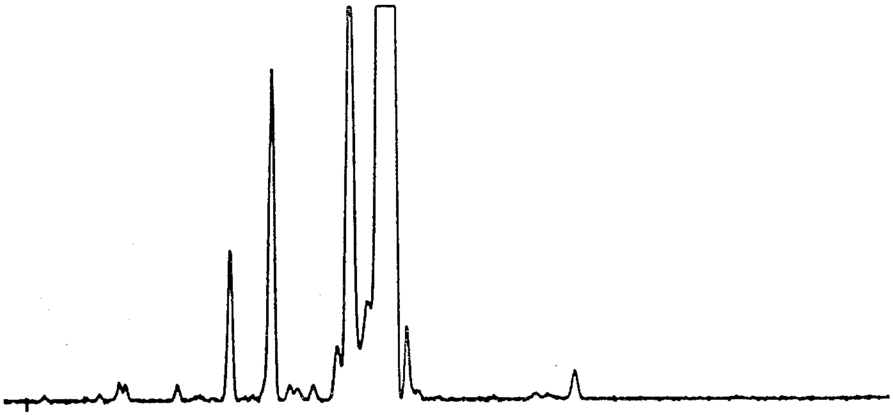
FIG. 2 - GLC PROFILE FOR EXAMPLE II BEST AVAILABLE COPY
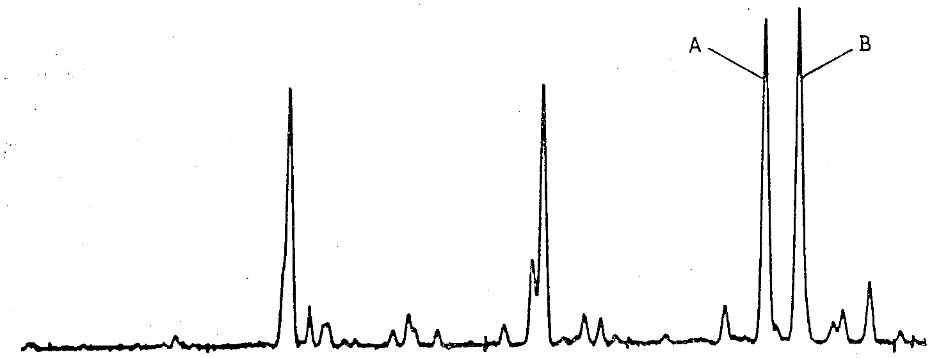
FIG. 3 - GLC PROFILE FOR EXAMPLE I(a)

BEST AVAILABLE COPY

BALSAMIC FRAGRANCE COMPOSITION AND PROCESS FOR PREPARATION

BACKGROUND OF THE INVENTION

1. Field of the Invention

The present invention relates to fragrance compositions having a highly desirable fruity, balsamic character and to the process for their preparation.

2. Description of the Prior Art

The resinous/oily products obtained from the needles and twigs of various conifers, such as the Canadian balsam (Abies Balsamea L.), have a pleasant balsam-like odor and their use is well known in the art of perfumery. These products are recognized to be good fixatives for perfumes used in soaps and the balsamic note is also highly desirable in the formulation of heavy, sweet, floral perfumes.

In spite of the desirable fragrance characteristics of these naturally derived products, there are problems associated with their use. The products are subject to the usual compositional variations present in natural substances and they can contain skin sensitizing agents. Also, the cost to produce consistently uniform, fragrance-grade products of this type is high. Synthetic products which have a balsamic character have therefore been much sought after by the fragrance industry.

Various derivatives of norbornane, that is, compounds containing the bicyclo[2.2.1]heptane moiety, are known to be useful as fragrances. Esters of methyl-substituted bicyclo[2.2.1]heptane- and heptene-carboxylic acids, for example, are described in U.S. Pat. No. 4,442,025 and disclosed to have fresh, natural odors. The compounds correspond to the structures

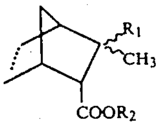

ENDO

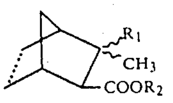

EXO in which the dotted line is a carbon-carbon single or double bond, $R_1$ is a hydrogen atom or methyl group and $R_2$ is an alkyl-or alkenyl group having 1–4 carbon atoms. Certain of the esters corresponding to the above formulas are indicated to have odors reminiscent of pine and cedar wood. There is also a general discussion of other norbornane derivatives in the reference.

To obtain the products of U.S. Pat. No. 4,442,025 the corresponding acids are first obtained and then esterified with the appropriate alcohol. 3,3-Dimethyl-bicyclo[2.2.1]heptane carboxylic acid is obtained by the peroxide-induced reaction of camphene and ethyl formate. Methyl-substituted bicyclo[2.2.1]heptene carboxylic acids are obtained by either reacting dicyclopentadiene with beta,beta-dimethylacrylylchloride or reacting cyclopentadiene with ethylcrotonate.

R. C. Kuder in an article entitled "Esters of Terpene-Derived Substituted Propionic Acids," *American Perfumer and Cosmetics,* 83(11):51–2(1968), indicates that the lower alkyl esters of 3,3-dimethyl-2-norbornanepropionic acid have distinctively pleasant odors. The esters are obtained by reaction of camphene with acetic anhydride to obtain the diadduct

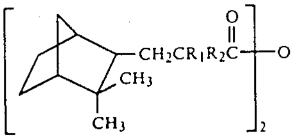

where $R_1$ and $R_2$ are hydrogen or alkyl. Reactions of this type are described in detail in U.S. Pat. Nos. 3,637,801, 3,641,144, and 3,689,537. After removal of excess acetic anhydride, the adduct can be converted by alcoholysis to the ester. Kuder indicates that the lower alkyl esters of 3,3-dimethyl-2-norbornanepropionic have very pleasant, fruity, berry-like odors with a woody character and that the methyl ester has a definite cedar wood undertone.

It would be highly desirable if balsamic fragrance products having pleasing fir needle notes were available. It would be even more advantageous if these products could be consistently produced utilizing readily available and economical starting materials.

SUMMARY OF THE INVENTION

These and other advantages are realized by the present invention wherein highly useful fragrance compositions having fruity, fir needle notes with the character of fir balsam absolute are produced. These compositions are obtained utilizing a multi-step procedure comprising:

(a) heating an ethylhaloacetate, camphene and di-t-butyl peroxide present in a molar ratio of 20:1:1 to 7.5:1:0.1 at a temperature from 135° C. to 180° C. and at atmospheric pressure up to 200 psig until essentially all of the camphene is reacted and distilling the mixture at atmospheric or slightly reduced pressure to remove substantially all of the unreacted ethylhaloacetate;

(b) adding from 1 to 5 moles of zinc and from 1 to 30 moles of water to the substantially ethylhaloacetate-free mixture and maintaining the temperature at 70° C. to 100° C. with vigorous agitation until reductive elimination is essentially complete;

(c) separating the organic phase from the aqueous phase; and (d) distilling the organic phase at a pressure of 5 mm Hg or below and collecting the fragrance composition which has a boiling range of 90° C. to 125° C. at 1 mm Hg.

BRIEF DESCRIPTION OF THE DRAWINGS

FIG. 1 represents the GLC profile of the balsamic fragrance composition obtained from step (d) of Example I.

FIG. 2 represents the GLC profile for the product obtained in accordance with the procedure described in Example 2 of U.S. Pat No. 3,637,801.

FIG. 3 represents the GLC profile for the essentially ethylchloroacetate-free intermediate porduct obtained from step (a) of Example I.

DETAILED DESCRIPTION OF THE DRAWINGS

FIG. 1 is a portion of the GLC profile for fraction No. 4 obtained from step (d) of Example I showing the major products present in the balsamic fragrance composition prepared in accordance with the present invention. The area percent report obtained for the balsamic

BEST AVAILABLE COPY fragrance composition showing the major components present is as follows:

| Retention Time (mins.) | Area | Area % |
|---|---|---|
| 11.957 | 660 | .33671 |
| 12.469 | 1005 | .51272 |
| 12.597 | 4037 | 2.05955 |
| 12.960 | 3575 | 1.82385 |
| 14.079 | 13665 | 6.97144 |
| 14.295 | 17321 | 8.83661 |
| 14.650 | 7236 | 3.69157 |
| 15.138 | 1524 | .77750 |
| 15.593 | 1339 | .68311 |
| 15.777 | 19326 | 9.85950 |
| 16.004 | 3530 | 1.80089 |
| 16.339 | 102875 | 52.48349 |
| 16.537 | 1828 | .93259 |
| 17.846 | 1383 | .70556 |
| 18.041 | 14751 | 7.52548 |
| 18.723 | 1959 | .99942 |
| TOTAL | 196014 | 100 |

Other components important to the overall aroma characteristics of the product are not listed in the above table as a result of the particular integration method used.

FIG. 2 is a portion of the GLC profile showing the major products obtained when camphene is reacted with acetic anhydride in accordance with Example 2 of U.S. Pat. No. 3,637,801. The product was distilled prior to GLC analysis and the fractionator head set to collect all materials boiling between 90° C. and 125° C. at 1 mm Hg—the same boiling range as the fragrance compositions of the present invention. The area percent report for the product showing the major components present is as follows:

| Retention Time (mins.) | Area | Area % |
|---|---|---|
| 14.066 | 3734 | 1.63477 |
| 14.665 | 8689 | 3.80409 |
| 15.611 | 1420 | .62168 |
| 15.792 | 17173 | 7.51843 |
| 16.033 | 3769 | 1.65009 |
| 16.439 | 191044 | 83.64006 |
| 16.593 | 1626 | .71187 |
| 19.061 | 957 | .41898 |
| TOTAL | 228412 | 100 |

It is apparent from a comparison of the GLC profile of FIG. 2 and the GLC profile of FIG. 1 that the compositions are substantially different. The composition of the present invention profiled in FIG. 1 contains numerous additional products not present in the product profiled in FIG. 2 and which are essential to obtain the desired balsamic fragrance odor characteristics. Both GLC analyses were carried out under identical conditions on a sample representing 95 percent or more of the total distillate. The GLC profiles represent approximately the same portion of the chromatographic trace.

FIG. 3 is a portion of the GLC profile showing the major products present in the intermediate mixture obtained by reacting ethylchloroacetate, camphene, and di-t-butyl peroxide in accordance with step (a) of Example I. The product was distilled prior to GLC analysis to remove substantially all of the unreacted ethylchloroactate. The profile represents that portion of the chromatogram between about 13 and 25 minutes (retention times). The area percent report obtained for the product showing the major components present is as follows:

| Retention Time (mins.) | Area | Area % |
|---|---|---|
| 2.988 | 813 | 1.56067 |
| 3.435 | 371 | .71219 |
| 3.895 | 495 | .95022 |
| 4.032 | 330 | .63348 |
| 4.943 | 566 | 1.08652 |
| 5.098 | 570 | 1.09420 |
| 5.420 | 3036 | 5.82804 |
| 14.384 | 8042 | 15.43778 |
| 14.659 | 716 | 1.37446 |
| 16.100 | 1291 | 2.47826 |
| 17.895 | 2525 | 4.84710 |
| 18.049 | 7058 | 13.54884 |
| 18.616 | 1078 | 2.06938 |
| 18.851 | 819 | 1.57219 |
| 20.648 | 907 | 1.74112 |
| 21.240 | 10000 | 19.19643 |
| 21.715 | 11513 | 22.10086 |
| 22.725 | 1963 | 3.76826 |
| TOTAL | 52093 | 100 |

DETAILED DESCRIPTION OF THE INVENTION

To obtain the compositions of this invention which have a balsamic fragrance, i.e., natural resinous background reminiscent of fir balsam absolute, a multi-step process is utilized.

In the first step of the reaction sequence, camphene (2,2-dimethyl-3-methylenebicyclo[2.2.1]heptane; 2,2-dimethyl-3-methylenenorbornane) is reacted with an ethylhaloacetate in the presence of an organic peroxide. Commercial camphene is employed for the reaction. Tricyclene, an equilibrium product present in commercial camphene in an amount from about 15 to 25 percent, does not interfere with the reaction. In fact, since the tricyclene reacts with ethylhaloacetate in the presence of peroxide in much the same manner as camphene, it is believed to be significant to the makeup of the composition and the desirable fragrance characteristics associated therewith. The ethylhaloacetate used in the reaction can be either the chloro or bromo derivative, i.e., ethylchloroacetate or ethylbromoacetate. Whereas di-t-butyl peroxide is the organic peroxide of choice, other organic peroxides having comparable decomposition temperatures can also be employed.

A molar excess of the ethylhaloacetate is utilized for the reaction. Most generally, the molar ratio of ethylhaloacetate to camphene is in the range 7.5:1 to 20:1. More generally, the molar ratio of ethylhaloacetate to camphene ranges from 9:1 to 12:1. The amount of peroxide used can vary but, most generally, about 0.1 to 1 mole peroxide is used per mole of camphene. In a more preferred embodiment of the invention, the molar ratio of camphene to peroxide is in the range 1:0.5 to 1:0.25. Particularly advantageous results are obtained when the molar ratio of reactants is about 10:1:0.3 (ethylhaloacetate:camphene:peroxide). All of the above molar calculations are made based on the weight of the camphene and assuming the camphene to be 100% 2,2-dimethyl-3-methylenebicyclo[2.2.1]heptane.

The reaction of the ethylhaloacetate and camphene is carried out in glass or glass-lined equipment at pressures ranging from atmospheric up to about 200 psig and at a temperature from about 135° C. up to about 180° C. More generally, however, the reaction is carried out at

BEST AVAILABLE COPY a temperature from 145° C. to 160° C. and pressure from 30 psig to 100 psig.

Progress of the reaction of the ethylhaloacetate and camphene can be conveniently monitored by following the amount of camphene reacted. This is readily accomplished by gas-liquid chromatographic (GLC) analysis of samples of the reaction mixture. When substantially all of the camphene is reacted, the reaction mixture is distilled to remove the excess ethylhaloacetate. This distillation is typically carried out under atmospheric conditions but vacuum distillation can be employed if desired. When substantially all of the ethylhaloacetate is removed, i.e., when the vapor temperature of the distillate at atmospheric pressure is about 150° C. when using ethylchloroacetate or about 175° C. when using bromoacetate, distillation is terminated and the residue (distilland) is suitable for further reaction in accordance with the process of this invention. The fragrance characteristics of the final product can be adversely affected if the distillation is allowed to proceed much above the boiling point of the ethylhaloacetate so that significant amounts of product(s) formed by the reaction and which contribute to the desirable fragrance qualities are removed. Failure to remove substantially all of the ethylhaloacetate will have an adverse effect on the economics of the process since it necessitates an increase in the amount of zinc used in the next step of the reaction. It can also have a detrimental effect on the fragrance qualities of the final product.

GLC analysis of the distilland shows that it is a mixture of products, however, the major constituents are halogenated ethyl-3,3-dimethylbicyclo[2.2.1]heptane-2-propanoates, such as ethyl-α-halo-3,3-dimethylbicyclo[2.2.1]heptane-2-propanoate which has the structural formula

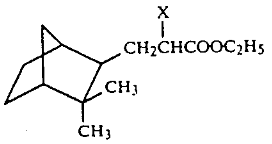

where X is chlorine or bromine.

The intermediate mixture thus obtained is utilized in the second step of the reaction wherein the mixture is reacted with zinc in the presence of water. This reaction results in the reductive elimination of halogen from the halogenated constituents, such as ethyl-α-halo-3,3-dimethylbicyclo[2.2.1]heptane-2-propanoate, which contain halogen in the alpha position. Reductive elimination reactions of alkyl halides are known and for ethyl-α-chloro-3,3-dimethylbicyclo[2.2.1]heptane-2-propanoate, a major constituent in the mixture, can be represented as follows:

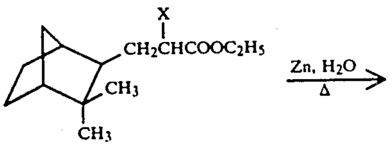

-continued

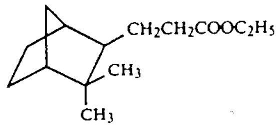

For the reductive elimination, zinc metal and water are added to the substantially ethylhaloacetate-free mixture obtained from the previous reaction step and the mixture is maintained at about 70° C. to about 100° C. with vigorous agitation until the reaction is essentially complete. The reductive elimination reaction is conveniently monitored by GLC by following the disappearance of the major halogenated constituents.

In one embodiment of the invention, the zinc and water are added separately. Zinc metal, preferably in powder or dust form, is most generally added first. The zinc metal can be washed with dilute acid or otherwise activated in accordance with conventional procedures prior to use. When the zinc addition is complete, water is added to the reaction mixture. Since both the addition of the zinc and the addition of the water are accompanied by an exotherm and some foaming, additions of these materials to the reaction mixture are generally made in small increments. It may also be advantageous to cool the reaction mixture to further facilitate these additions. When addition of the water is complete, the mixture is then maintained at 70° C. to 100° C. and, more preferably, from 85° C. to 100° C. Vigorous agitation is advantageous to obtain efficient contact of the reactants.

Since the reaction mixture is typically a viscous mass and, in some cases, may even form an emulsion, it may be advantageous to add an inert organic solvent or diluent for the reductive elimination reaction. This facilitates reaction since it solubilizes the organic materials, provides better contact with the zinc metal, and maintains the reaction mixture in a more fluid state. Organic solvents which are useful should be inert to the reaction conditions and not miscible with water. They should also have boiling points above 100° C. at atmospheric pressure and below the boiling range of the fragrance composition, i.e., less than 90° C. at 1 mm Hg. Illustrative organic solvents which can be used include toluene, xylene, mineral spirits, Super Naphtholite (trademark), amyl acetate, and the like. In one embodiment of the invention, aromatic hydrocarbons, such as toluene and xylene, are employed for the reductive elimination reaction. If an organic solvent is used, it is generally employed in an amount from about 5 to 30 percent of the reaction mixture. More preferably, the organic solvent will constitute from 10 to 20 percent of the mixture.

The amount of zinc employed for the reaction can range from about 5:1 to about 1:1 (molar ratio of Zn to intermediate mixture). Calculation of the molar ratio of the intermediate mixture is made assuming it to be 100% ethyl-α-chloro-3,3-dimethylbicyclo[2.2.1]heptane-2-propanoate. Most preferably, the molar ratio of the zinc:intermediate ranges from 1.5:1 to 1:1. The molar ratio of water to intermediate can range from 30:1 to 1:1 but most generally is in the range 15:1 to 5:1.

When essentially all of the halogenated constituents are reacted, heating is terminated. After the reaction mixture has been allowed to cool somewhat, the organic phase containing the desired fragrance composi-

BEST AVAILABLE COPY tion and the aqueous phase containing unreacted zinc, dissolved and undissolved zinc salts, and other by-products of the reaction are separated. While it is not necessary, the reaction mixture can be filtered to remove insoluble salts and unreacted zinc prior to separation of organic and aqueous phases. If an organic solvent was employed in the reductive elimination step, separation is conveniently accomplished by allowing the reaction mixture to separate and by either decanting or siphoning off the organic phase or by draining the aqueous phase from the bottom of the reactor. If no diluent was used in the reductive elimination step or if the amount of diluent is not sufficient to achieve efficient separation, organic solvent is added to the reaction mixture and intimately contacted therewith. The separation is then carried out in the usual manner. Any organic solvent immiscible with water and which does not have a boiling point within the boiling range of the fragrance composition can be utilized for this purpose. These solvents can be the same or different than the solvent used for the reductive elimination. Aromatic hydrocarbons such as benzene, xylene, and toluene are advantageously used for this purpose.

After separation, the organic phase which upon GLC analysis is shown to be a mixture of products, is distilled to obtain the useful balsamic fragrance composition of the invention. Distillation is carried out at reduced pressure—typically at a pressure of 5 mm Hg or below and, more usually, from about 0.1 to about 2 mm Hg. Conventional distillation apparatus and procedures are utilized. To obtain a composition having the desired balsamic fragrance qualities, i.e., having a character reminiscent of fir balsam absolute with an especially desirable diffusive fruity, fir needle top note, the fraction boiling in the range about 90° C. to about 125° C. at a pressure of 1 mm Hg is collected. As will be evident to those skilled in the art, the boiling range of the product will be different at pressures other than 1 mm Hg. Material outside the specified boiling range does not have the desired fragrance characteristics. The fragrance composition thus obtained is a colorless to light yellow liquid having a specific gravity (25/25° C.) in the range 0.9750–0.9850, flashpoint (COC) of 266° F., saponification value (AOCS Method Tl 1a-64) of 200-212, and acid value (AOCS Method Te 1a-64) less than 2. The product has a pleasing balsamic aroma (resinous background) reminiscent of fir balsam absolute. The composition also has distinctive fruity and cistus/-labdanum notes.

The balsamic fragrance compositions of this invention are useful for the formulation of fragranced products such as perfumes, colognes, shampoos, deodorants, shaving creams and gels, body lotions and creams, detergent and bar soaps, air fresheners, room sprays, pomanders, candles, and the like. The amount of the composition used depends on the particular formulation involved and whether it is the sole fragrance material used or, as is more usually the case, if it is used in conjunction with other fragrance materials. In some instances, as little as 0.05 percent of the composition is sufficient to impart a clearly detectable balsamic odor to a formulation. For most applications, however, the composition is utilized in an amount from 0.1 up to about 10 weight percent of the finished formulation.

The present compositions are readily compatible with other fragrance materials including essential oils, resinoids, absolutes, and a wide variety of other synthetic compounds. They are also compatible with solvents and other auxilliary agents used in the preparation of fragrance formulations, such as ethanol, isopropanol, diethylene glycol, monoethyl ether, diether phthalate, and the like.

The present fragrance compositions are useful for the preparation of floral and a wide variety of other formulations and in this connection they are advantageously utilized in conjunction with but not limited to jasmin odorants, rose odorants, orangeflower odorants, lily odorants, fruity odorants, and odorants which impart green and woody notes. Various fragrance compounds which can be formulated with the balsamic compositions of the invention include: citronellol; hydroxycitronellol; linalool; tetrahydrolinalool; coumarin; vanillin; geraniol; rhodinol; citral; nerol; eugenol; isoeugenol; farnesol; borneol; phenylethyl alcohol; phenoxyethanol; phenylacetic acid; methyl phenylacetate; methyl phenylethyl ether; phenylacetaldehyde; phenylacetaldehyde dimethyl acetal; cinnamyl acetate; cinnamyl tiglate; hexylcinnamic aldehyde; cinnamyl formate; ethyl cinnamate; benzyl acetate; benzyl salicylate; jasmone; iso-jasmone; hydroxycitronellal; linalyl acetate; methyl anthranilate; indole; hydratropic aldehyde; cis-3-hexenal; cis-3-hexenol; trans-2-hexenal; nonadienyl acetate; phenoxyacetaldehyde; gamma-undecalactone; phenylethyl acetate; benzaldehyde; hexyl benzoate; trans-anethole; amyl propionate; cedryl acetate; t-butyl cyclohexyl acetate; ionones; methyl ionones; 4-carbethoxy-2-ethyl-5-methyl-2,3-dihydrofuran; 4-carbethoxy-2-ethyl-2,5-dimethyl-2,3-dihydrofuran; 4-carbethoxy-2-propyl-5-methyl-2,3-dihydrofuran; ethylene brassylate; ethylene dodecanedioate; and the like.

The following examples illustrate the invention more fully but are not intended as a limitation on the scope thereof. In these examples, all parts and percentages are on a weight basis unless otherwise indicated.

GLC analyses were carried out using a Hewlett Packard Model 5890 gas chromatograph equipped with a Model 3393A integrator. A 30 meter DB 5 capillary column (0.32 mm I.D.) was employed using a 100:1 split mode helium carrier gas and temperature of 150°-200° C. at 2° C. per minute. One microliter of sample (50% in diethyl ether) was used. The integration method employed the Unigram option and the following run parameters were used:

ZERO=0
ATT $\hat{2}$=0
CHT SP=0.5
AR REJ=0
THRSH=0
PK WD=0.04

EXAMPLE I (a) Reaction of Camphene and Ethylchloroacetate:

To a clean, dry, agitated glass-lined reaction vessel were charged 5,313 parts ethylchloroacetate, 587 parts molten camphene, and 189 parts di-t-butyl peroxide (molar ratio ethylchloroacetate:camphene:peroxide 10:1:0.3). A vacuum was applied and the reactor isolated. The reaction mixture was then slowly heated to 150°-155° C. The reactor was vented as necessary into a scrubber containing aqueous caustic so that the pressure did not exceed 70 psi. After 4 hours, GLC analysis of the reaction mixture confirmed that substantially all of the camphene was reacted.

Unreacted ethylchloroacetate was distilled from the reaction mixture by slowly releasing the pressure and, when the distillation slowed, slowly applying a vacuum of 26 inches. When no further distillate was being removed, the mixture was cooled to 50° C. and the vacuum released with nitrogen. Chlorine analysis showed the product to contain 9% chlorine. FIG. 3 represents a portion of the GLC profile for the reaction product of the intermediate mixture thus obtained.

(b) Reductive Elimination Reaction:

Toluene (300 parts) was added to the essentially chloroacetate-free product obtained from step (a) while vigorously agitating the mixture. Zinc powder was then added in small portions so that the temperature did not exceed about 100° C. and excessive foaming was avoided. After a total of 283 parts zinc powder was added, the reactor was heated to 100° C. Water (1,128 parts) was then added over a period of about 1 hour at a rate such that excessive refluxing was avoided. The molar ratio of zinc:intermediate:water for the reaction was 1:1:14. When the addition of water was complete, the mixture was heated at 100° C. and sampled at regular intervals for GLC analysis. When GLC analysis showed virtually all of the major chlorinated substituents to be consumed, i.e., the two peaks occurring at retention times of 21.240 and 21.715 minutes and identified as A and B in FIG. 3, agitation was stopped and the reaction mixture was cooled to 50° C. Chlorine analysis showed the product to contain 0.35% chlorine.

(c) Separation of Aqueous and Organic Phases:

The viscous mixture obtained from step (b) was allowed to stand until the aqueous and organic phases separated. The organic (top) layer was then siphoned from the reactor.

(d) Distillation:

A portion of the organic phase obtained from step (c) was transferred to a distillation vessel and distilled at 110° C. under atmospheric pressure to remove the toluene and any residual water. The distilland (344 grams) was then vacuum distilled using a 2 foot adiabatic column with metal helices to obtain the balsamic fragrance composition. Distillation cuts collected during the vacuum distillation were as follows:

| Fraction | Weight (Grams) | Vapor Temperature (°C.) | Vacuum (mm Hg) |
|---|---|---|---|
| 1 | 1.2 | 27-49 | 1.8 |
| 2 | 3.3 | 48-79 | 0.8-2.0 |
| 3 | 2.0 | 81-95 | 1.7-2.0 |
| 4 | 325.0 | 94-130 | 1.8-2.0 |

Fraction No. 4 had a pleasing balsamic aroma and was retained. The product was a colorless liquid having a specific gravity (25/25° C.) of 0.9795, saponification value 205.9, and acid value of 1.35. The product boiled in the range 90°-125° C. at 1 mm Hg and GLC analysis of the composition showed it to be a mixture of products. FIG. 1 represents a portion of the GLC profile for fraction No. 4, the highly desirable balsamic fragrance composition.

The fragrance composition (fraction No. 4) was characterized as having a pleasing balsamic aroma reminiscent of fir balsam absolute with an especially desirable diffusive fruity, fir needle top note, and was used to scent various soap, detergent, and household products. For example, fragranced soap bars were prepared using the Mazzoni process. A commercial non-scented soap stock was employed to which water was added to maintain the desirable plasticity. The fragrance composition (1 percent by weight) was added and thoroughly blended before the soap stock was refined and extruded (plodded) in tubular form. Soap bars were then stamped from sections of the extruded tube. The scented bars had a pleasing balsamic odor similar to that of the fragrance composition.

The balsamic fragrance prepared above was also added at a 1 weight percent level to a typical herbal perfume base to impart a desirable balsamic note and improve the overall odor character.

The balsamic aroma chemical was also blended into a cosmetic grade talc at a concentration of 0.1 weight percent. A portion of the fragranced talc was then subjected to ultraviolet radiation for 8 hours and no noticeable discoloration or change in the pleasing balsamic odor character was observed. Similarly, a pleasantly fragranced detergent was obtained by adsorbing 0.1 weight percent of the balsamic fragrance composition on a commercially available stock. The resulting detergent showed no evidence of discoloration or deterioration and the detergent odor was effectively reduced. There was no noticeable change in odor or color of either the fragranced talc or detergent upon subjecting the products to an oven stability test wherein they were heated at 50° C. for a period of two weeks.

EXAMPLE II

In accordance with the procedure of Example 2 of U.S. Pat. No. 3,637,801, 676 mls acetic anhydride was charged to a glass reactor and heated to 140° C. A mixture of 68 grams camphene (0.5 mole), 6.57 grams (0.09 mole) di-t-butyl peroxide, and 149 ml acetic anhydride, to which 13 mls of acetic acid was added to facilitate solubilization of the camphene, was slowly added to the reactor over a 4-hour period and then refluxed for about 20 hours. The mole ratio of acetic anhydride to camphene for the reaction was 17:1. After removal of the excess acetic anhydride by distillation, 500 mls ethanol and 0.5 mls conc. sulfuric acid were then added and the mixture refluxed until GLC analysis indicated alcoholysis to be essentially complete. The mixture was neutralized with sodium carbonate, filtered, and vacuum distilled. The fraction boiling over the range 90°-125° C. at 1 mm Hg was collected. FIG. 3 represents a portion of GLC profile obtained for the product. Whereas this product had a faint berry, labdanum character, it did not have the intense and highly diffusive natural fir needle, balsamic character of the product prepared in accordance with the process of Example I.

EXAMPLE III

To demonstrate the ability to vary certain aspects of the process, 4501.8 grams ethylchloroacetate was charged to a reactor and a mixture of 618 grams camphene and 162 grams di-t-butyl peroxide added thereto at reflux over a 6-hour period and then refluxed for an additional 12 hours. (Molar ratio ethylchloroacetate:camphene:peroxide 10:1:0.3). Excess ethylchloroacetate was then removed from the reaction mixture and 478.7 grams (7.32 moles) zinc powder and 1200 mls water added. (Molar ratio Zn:intermediate:water 2:1:18). An immediate exotherm was observed. Upon completion of the reductive elimination reaction, 214.5 mls acetic acid was added with stirring. The mixture was then filtered to remove excess zinc and the organic and aqueous layers separated. The organic portion was distilled and after removal of the top cuts containing water, acetic acid, and other low boiling materials, the fraction boiling at 90° C.-125° C. at 1 mm Hg was col-

BEST AVAILABLE COPY lected. The product had a pleasing balsamic odor and GLC profile comparable to that obtained for the product of Example I.

EXAMPLE IV

To further demonstrate the versatility of the process, different procedures were employed to carry out the reductive elimination step. For all of these reactions, the intermediate mixture used was obtained in accordance with the procedure of Example I step (a). For the first reaction, 129.9 grams (0.39 mole) of the substantially ethylchloroacetate-free intermediate mixture containing 23 percent toluene was charged to a reactor with 100 mls water and heated to 60° C. Zinc powder (25.5 grams; 0.39 mole) was then added and the mixture slowly heated to 90° C. Heating was continued for about 6 hours, and after filtering to remove unreacted zinc and other insoluble materials, the procedures of steps (c) and (d) of Example I were followed to obtain the balsamic fragrance composition.

In another variation, 100 grams (0.39 mole) of the essentially ethylchloroacetate-free intermediate mixture was combined with 100 mls water and heated to 100° C. Zinc metal (25.5 grams; 0.39 mole) was then added and the heating continued for 16 hours. After removal of unreacted zinc and other insolubles by filtration, the procedures of steps (c) and (d) of Example I were followed to obtain the balsamic fragrance composition.

For another reductive elimination, 100 grams (0.39 mole) of the essentially ethylchloroacetate-free intermediate mixture was combined with 100 mls water and heated to 80° C. Zinc metal 25.5 grams (0.39 mole) was added and the mixture heated at 80° C. for 2 hours and at 100° C. for 16 hours. After filtering to remove unreacted zinc and other insoluble materials, the product was worked up in accordance with steps (c) and (d) of Example I to obtain the balsamic fragrance composition.

In yet another procedure, 12.6 grams (0.2 mole) zinc dust was combined with 500 mls water and heated to 80° C. Two mls conc. hydrochloric acid was then added and the mixture heated for one hour. Fifty grams (0.2 mole) of the essentially ethylchloroacetate-free intermediate mixture was then added to the flask and heated with stirring for about 16 hours. The product was worked up in accordance with steps (c) and (d) of Example I after filtration to obtain the fragrance composition.

Although the yield of the desired product varied, in all of the above instances the resulting composition had a balsamic odor and GLC profile comparable to that obtained for the product of Example I.

We claim:

1. A process for preparing a fragrance composition comprising the steps of:
   (a) heating an ethylhaloacetate, camphene and di-t-butyl peroxide present in a molar ratio of 20:1:1 to 7.5:1:0.1 at a temperature from 135° C. to 180° C. and at atmospheric pressure up to 200 psig until essentially all of the camphene is reacted and distilling the mixture at atmospheric or slightly reduced pressure to remove substantially all of the unreacted ethylhaloacetate;
   (b) adding from 1 to 5 moles of zinc, per mole of intermediate, and from 1 to 30 moles of water, per mole of intermediate, to the substantially ethylhaloacetate-free mixture and maintaining the temperature at 70° C. to 100° C. with vigorous agitation until reductive elimination is essentially complete;
   (c) separating the organic phase from the aqueous phase; and
   (d) distilling the organic phase at a pressure of 5 mm Hg or below and collecting the fragrance composition which has a boiling range of 90° C. to 125° C. at 1 mm Hg.

2. The process of claim 1 wherein for step (a) the molar ratio of ethylhaloacetate:camphene:di-t-butyl peroxide is from 9:1:0.25 to 12:1:0.5, the temperature is from 145° C. to 160° C., and the pressure is from 30 psig to 100 psig.

3. The process of claim 2 wherein the ethylhaloacetate is ethylchloroacetate.

4. The process of claim 1 wherein for step (b) the water is added after addition of the zinc.

5. The process of claim 4 wherein the reductive elimination reaction (b) is carried out in the presence of 5 to 30 weight percent, based on the weight of the total reaction mixture, of an inert organic solvent.

6. The process of claim 4 wherein the molar ratio of zinc to intermediate is from 1.5:1 to 1:1 and the molar ratio of water to intermediate is 15:1 to 5:1.

7. The fragrance product produced in accordance with the process of claim 1 and further characterized as having a fruity, pine needle note with the character of fir balsam absolute.

8. The process for augmenting or enhancing the aroma of a fragrance composition or fragranced article comprising the step of adding an aroma augmenting or enhancing amount of the product produced in accordance with the process of claim 1.

* * * * *